United States Patent [19]

Ruch

[11] Patent Number: 5,676,494
[45] Date of Patent: Oct. 14, 1997

[54] PARTICLE INJECTOR FOR FLUID SYSTEMS

[75] Inventor: Jeffrey F. Ruch, Bethel Park, Pa.

[73] Assignee: The United States of America as represented by the Department of Energy, Washington, D.C.

[21] Appl. No.: 614,753

[22] Filed: Mar. 14, 1996

[51] Int. Cl.⁶ .................................................. B65G 53/14
[52] U.S. Cl. .................................................. 406/152; 406/153
[58] Field of Search .................................. 406/151, 152, 406/153, 108, 122, 92, 144, 137

[56] References Cited

U.S. PATENT DOCUMENTS

| | | | |
|---|---|---|---|
| 4,005,806 | 2/1977 | Baldwin | 406/137 |
| 4,320,995 | 3/1982 | Tennes et al. | 406/122 |
| 4,642,944 | 2/1987 | Fairhurst et al. | 406/137 |
| 5,195,850 | 3/1993 | Davis et al. | 406/144 |
| 5,447,394 | 9/1995 | Shepard | 406/144 |

*Primary Examiner*—Gary C. Hoge
*Attorney, Agent, or Firm*—Virginia B. Caress; William R. Moser; Paul A. Gottlieb

[57] ABSTRACT

A particle injector device provides injection of particles into a liquid stream. The device includes a funnel portion comprising a conical member having side walls tapering from a top opening (which receives the particles) down to a relatively smaller exit opening. A funnel inlet receives a portion of the liquid stream and the latter is directed onto the side walls of the conical member so as to create a cushion of liquid against which the particles impact. A main section of the device includes an inlet port in communication with the exit opening of the funnel portion. A main liquid inlet receives the main portion of the liquid stream at high pressure and low velocity and a throat region located downstream of the main liquid inlet accelerates liquid received by this inlet from the low velocity to a higher velocity so as to create a low pressure area at the exit opening of the funnel portion. An outlet opening of the main section enables the particles and liquid stream to exit from the injector device.

10 Claims, 1 Drawing Sheet

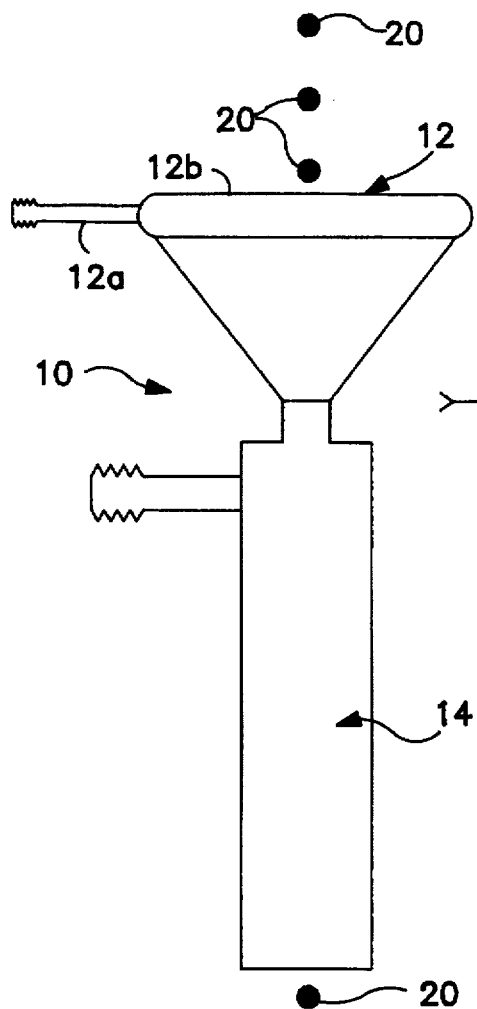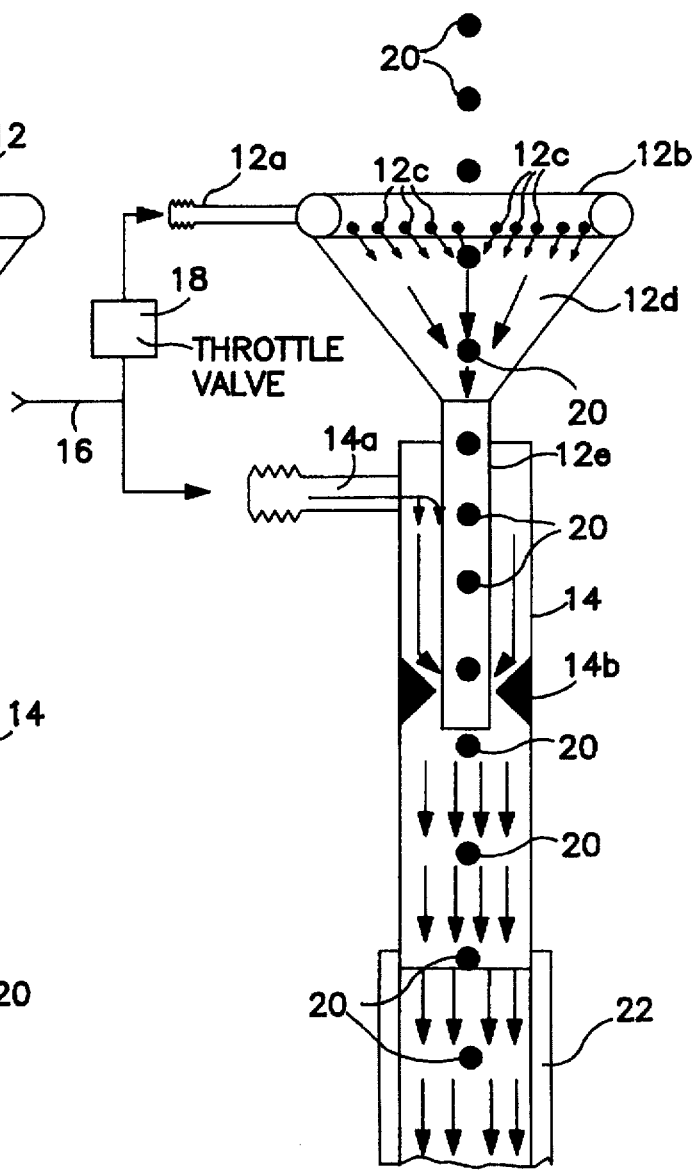

PARTICLE INJECTOR FOR FLUID SYSTEMS

BACKGROUND OF THE INVENTION

1. Field of Invention

The present invention relates to methods and devices for injecting particle into a moving fluid system.

2. The Prior Art

There are a number of applications requiring the injection particles into a moving fluid and, although the invention is particularly concerned with, and is described below in the context of, particle injection in connection with the calibration of inline optical particle counters, additional applications are also of interest here. These other applications include the injection of particles to provide particle cooling, particle heating, transporting or conveying of the particles and particle coating.

In order to properly calibrate an optical or laser particle counter, particles of a known size must pass through the optical chamber of the counter. This is easy to achieve with optical particle counters which count particles in air. However, when particles are being counted in a liquid, it becomes difficult to inject, calibrated (sized) particles. Conventionally, a "dead leg" or branch off of the fluid system is provided which, through the use of suitable valving, can be opened so as to enable the insertion of particles into the flow system. However, this approach presents problems because the particles are not spaced from one another during the travel thereof and thus can enter the optical counting chamber at the same time in a mass, thereby producing large errors in the size of the particles being counted. Many optical particle counters are also sensitive to the particle velocity or the liquid velocity. Particles that are moved or clumped together will tend to accelerate to the velocity of the liquid and this will also introduce an error in the size of the corresponding particle counted. It is also desirable to be able to accurately determine the actual number of particles detected by the particle counter so that this number can be compared with the number of particles introduced.

Considering in more detail the uses mentioned above for a particle injector for injecting particles into a moving fluid system, cooling or heating of the particles can be accomplished simply by injecting the particles into a cold or hot fluid. Transporting of the particles using specialized techniques can be necessary when the particles are required at another location but are fragile and thus difficult to handle and transport. Coating of particles can be carried out by injecting the particles into a coating liquid and then transferring the particles to a further operation or station in an overall coating or other process.

SUMMARY OF THE INVENTION

In accordance with the invention, a particle injector is provided which enables particles to be injected into a moving liquid system without valving off a "dead leg" in the system as done in the prior art.

According to a preferred embodiment thereof, the particle injector device comprises: an input section comprising an inlet opening for receiving the particles; first inlet means for receiving a first portion of the liquid stream and for directing said first portion so as to form a cushion for the particles received through said inlet opening; and an outlet opening for the particles and the first portion of the liquid stream; and a flow control section comprising an inlet opening providing communication between the flow control section and the outlet opening of the input section, further inlet means for separately receiving the remaining portion of the liquid stream and for directing that remaining portion so as to produce a flow stream made up of said remaining portion, said particles and said first portion, flow control means for accelerating said flow stream so produced so as to create a low pressure area at the outlet opening of the input section, and an outlet port for the flow stream.

Preferably, the input section comprises a funnel member having slant side walls tapering inwardly from the inlet opening to the outlet opening. The first inlet means preferably comprises an inlet connection, an annulus disposed around the inlet opening of the input section and defining an annular volume in communication with the inlet connection, and a plurality of equally spaced, circumferential disposed, inwardly directed openings therein for directing the first portion of the liquid stream against said side walls of the funnel member so as to produce said cushion. Advantageously, a throttle valve is connected upstream of the inlet connection for limiting the flow.

The flow control section preferably comprised a cylindrical member having a top opening forming said inlet opening of the flow control section and the funnel member preferably includes a lower tubular portion extending down into said top opening. Advantageously, the further inlet means comprises an inlet connector located at a top portion of the cylindrical member. In a preferred implementation, the tubular portion of the funnel member has a distal end and the flow control means comprises a throat region disposed below the inlet connector and, in a specific embodiment, between the inlet connector and the distal end of the tubular portion.

Other features and advantages of the invention will be set forth in, or apparent from, the following detailed description of the preferred embodiment of the invention.

BRIEF DESCRIPTION OF THE DRAWINGS

FIG. 1 is side elevational view of a particle injector constructed in accordance with a preferred embodiment of the invention; and FIG. 2 is a cross sectional view of the particle injector of FIG. 1, including an additional downstream connection.

DESCRIPTION OF THE PREFERRED EMBODIMENTS

Referring to FIG. 1, a side elevational view is shown of a particle injector constructed in accordance with a preferred embodiment of the invention. The particle injector, which is generally denoted 10, includes a funnel portion or funnel 12 of substantially conical shape and a main body portion or body 14 of generally cylindrical shape, although other shapes are, of course, feasible.

As shown in FIG. 2, which is cross sectional view of the injector 10, funnel portion 12 includes a liquid inlet 12a which opens into an annulus or ring section 12b having a plurality of inlet openings or apertures 12c therein, a conical section 12d and tubular section 12e. The liquid supplied to liquid inlet 12a is tapped off from a main liquid flow stream system, indicated at 16, through a throttling valve 18.

As indicated FIGS. 1 and 2, the particles to be injected which are denoted 20, are supplied along the vertical axis of injector 10 and, as shown in FIG. 2, the liquid flowing through openings 12c onto the funnel section 12d of funnel 12 creates or produces a cushion in which particles 20 land.

This liquid also keeps air from being drawn into the main liquid stream. After exiting from the funnel section, the particles 20 and the associated liquid flow through tubular section into the main body 14.

Main body 14 includes a main liquid inlet 14a which, as indicated in FIG. 2, receives the main liquid flow, i.e., the remainder of the liquid that does not flow through throttle valve 18. A throat portion, i.e., a portion of reduced diameter, denoted 14b, creates a venturi in the region of the outlet of funnel tube 12e. It will be understood that in the region of liquid inlet 14a, the liquid is at high pressure and low velocity and thus creates a low pressure area at the bottom of funnel 12. This low pressure area draws the liquid and the particles 20 from the funnel 12 into the center of the main fluid flow in main body section 14 and accelerates the particles 20 to the velocity of the liquid. As illustrated, in this embodiment, the lower end of the main body section 14 opens into a further cylinder 22 which can, for example, be an input part of an optical counter.

It will be appreciated that in using an optical counter it is important to know the fluid flow rate because the particle velocity can change the recorded size of the particle. In other words, a different, inaccurate particle size may be recorded when the velocity of the particles changes from that for which the counter is calibrated. By using the particle injector of the invention, a metered pump flow can be used to pump the liquid and because all of the liquid is at the same volume at the outlet of injector 10, the metered flow rate remains constant. Thus, if the area of the optical chamber is known (and this can be readily determined), the velocity of the fluid can be calculated.

Using the particle injector of the invention as a particle handling device provides a number of important advantages over other handling techniques. For example, the injector prevents chemical contamination of the particles such as can occur when chemical contaminants directly contact the particles. In this regard, a liquid which is compatible with the particles can be used so that no adverse chemical contamination can occur. Additionally, additional processing or treatment of the particles, such as heating, cooling or coating, can be carried out as the particles are transported to the next station or next processing stage. For example, a hard coating provided from the liquid can be applied to fragile particles so that the particles are easier to handle or process.

The invention enables particles and materials to be injected into a moving liquid stream on a continuous basis, and the handling of particles of many materials can be greatly enhanced by this capability. Further, as explained above, the invention enables optical counters that are used in liquid systems to be correctly calibrated using calibrated particles and the same liquid as the working liquid. This removes the need for many of the correction factors that normally must be applied as well as eliminates much of the uncertainty associated with optical counter calibration. It will be evident that the preferred construction of the invention described above can be manufactured as a few easily machinable pieces that can be assembled by welding, by mechanically securing threaded pieces together or using other assembly techniques. The particle injector can be made of glass, a suitable plastic or any machinable metal that is compatible with the working fluid flowing therethrough.

Although the present invention has been described to specific exemplary embodiments thereof, it will be understood by those skilled in the art that variations and modifications can be effected in these exemplary embodiments without departing from the scope and spirit of the invention.

What is claimed is:

1. A particle injector device for injecting particles into a liquid stream, said device comprising:

An input section comprising an inlet opening for receiving the particles; first inlet means for receiving a first portion of the liquid stream and for directing said first portion so as to form a cushion for the particles received through said inlet opening; and an outlet opening for the particles and said first portion of said liquid stream; and A flow control section comprising an inlet opening providing communication between said flow control section and the outlet opening of said input section; further inlet means comprising an inlet connector disposed at a top portion of said flow control section for separately receiving the remaining portion of said liquid stream and for directing said remaining portion so as to create a vertical flow stream comprising said remaining portion, said particles and said first portion; flow control means for accelerating said flow stream so as to create a low pressure area at said outlet opening of said input section, and an outlet port for said flow stream.

2. A device as claimed in claim 1 wherein said input section comprises a funnel member having slant side walls tapering inwardly from said inlet opening to said outlet opening.

3. A device as claimed in claim 2 wherein said first inlet means includes an inlet connection, an annulus disposed around said inlet opening of the input section and defining an annular volume in communication with said inlet connection, and a plurality of equally spaced, circumferential disposed, inwardly directed openings therein for directing said first portion of the liquid stream against said side walls of said funnel member.

4. A device as claimed in claim 3 further comprising a throttle valve connected upstream of said inlet connection.

5. A device as claimed in claim 2 wherein said flow control section comprises a cylindrical member having a top opening forming said inlet opening of said flow control section and a bottom opening forming said outlet port, and wherein said funnel member includes a lower tubular portion extending down into said top opening.

6. A device as claimed in claim 5 wherein said tubular portion of said funnel member has a distal end and said flow control means comprises a throat region disposed between said inlet connector and said distal end of said tubular portion.

7. A device as claimed in claim 1 wherein said flow control means comprises a throat region disposed downstream of said inlet connector.

8. A particle injector device for injecting particles into a liquid stream, said device comprising: a funnel portion, for receiving the particles, comprising a conical member having side walls tapering from a top opening down to a relatively smaller exit opening, funnel inlet means for receiving a portion of the liquid stream, and directing means for directing said portion of the liquid stream onto the side walls of said conical member so as to create a cushion of liquid against which the particles impact; and a cylindrical main portion including an inlet port in communication with the exit opening of said funnel portion, main liquid inlet means for receiving a main portion of the liquid stream at high pressure and low velocity, said main liquid inlet means comprising an inlet connector disposed at a top portion of said cylindrical main portion for separately receiving said main portion of said liquid stream and for directing said main portion so as to create a substantially vertical flow stream, and a throat region downstream of said main liquid inlet means for accelerating liquid received by said main liquid inlet means from said low velocity to a higher velocity so as to create a low pressure area at the exit opening of the funnel portion, and an outlet opening for the particles and liquid stream.

9. The device as claimed in claim 8, wherein said directing means comprises a hollow annulus disposed around the top opening of the funnel portion, said annulus including an interior volume in communication with said main liquid inlet means and inwardly facing circumferentially spaced openings for directing liquid from said volume onto said side walls of said conical member.

10. The device as claimed in claim 8, further comprising a throttle valve connected upstream of said funnel inlet means.

* * * * *